US012558389B1

(12) United States Patent
Tran

(10) Patent No.: US 12,558,389 B1
(45) Date of Patent: Feb. 24, 2026

(54) PLANT-BASED EXTRACT COMPLEX COMPOSITION HAVING THE PROPERTIES FOR SUPPORTING THE RELIEF OF MUSCULOSKELETAL PAIN, ANTIBACTERIAL AND ANTI-INFLAMMATORY AND PROCESS OF MANUFACTURING THE SAME

(71) Applicant: Dang Huy Tran, Ho Chi Minh (VN)

(72) Inventor: Dang Huy Tran, Ho Chi Minh (VN)

(73) Assignee: Dang Huy Tran, Ho Chi Minh (VN)

( * ) Notice: Subject to any disclaimer, the term of this patent is extended or adjusted under 35 U.S.C. 154(b) by 0 days.

(21) Appl. No.: 19/275,921

(22) Filed: Jul. 21, 2025

(51) Int. Cl.
| | |
|---|---|
| *A61K 36/00* | (2006.01) |
| *A61K 9/00* | (2006.01) |
| *A61K 9/51* | (2006.01) |
| *A61K 31/216* | (2006.01) |
| *A61K 36/258* | (2006.01) |
| *A61K 36/534* | (2006.01) |
| *A61K 36/535* | (2006.01) |
| *A61K 36/537* | (2006.01) |
| *A61K 36/54* | (2006.01) |
| *A61K 36/61* | (2006.01) |
| *A61K 47/10* | (2017.01) |
| *A61K 47/18* | (2017.01) |
| *A61K 47/26* | (2006.01) |
| *A61K 47/32* | (2006.01) |
| *A61P 29/00* | (2006.01) |

(52) U.S. Cl.
CPC .......... *A61K 36/258* (2013.01); *A61K 9/0017* (2013.01); *A61K 9/5176* (2013.01); *A61K 31/216* (2013.01); *A61K 36/534* (2013.01); *A61K 36/535* (2013.01); *A61K 36/537* (2013.01); *A61K 36/54* (2013.01); *A61K 36/61* (2013.01); *A61K 47/10* (2013.01); *A61K 47/18* (2013.01); *A61K 47/26* (2013.01); *A61K 47/32* (2013.01); *A61P 29/00* (2018.01)

(58) Field of Classification Search
None
See application file for complete search history.

*Primary Examiner* — Russell G Fiebig

(57) ABSTRACT

A plant-based extract complex composition having the properties for supporting the relief of musculoskeletal pain, antibacterial and anti-inflammatory is obtained from the process of forming a homogeneous mixing mixture by mixing in a specific order into a container including (A) a ginseng extract solution having a first percentage (%) by weight, (B) a medicinal herbs extract solution having a second percentage (%) by weight, (C) a plant-derived nanovesicles ingredient component having a third percentage (%) by weight, (D), a plant-derived essential oils ingredient having a fifth percentage (%) by weight (E) a methyl salicylate component having a fourth percentage (%) by weight, (F) an excipients component having a sixth percentage (%) by weight, and (G) water to create a mixture.

6 Claims, 1 Drawing Sheet

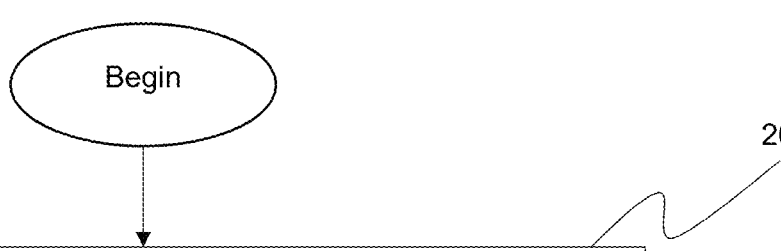

Begin

201

Preparing material including: a ginseng extract solution having a first percentage (%) by weight, a medicinal herbs extract solution having a second percentage (%) by weight, a plant-derived nanovesicles ingredient having a third percentage (%) by weight, a methyl salicylate component having a fourth percentage (%) by weight, a plant-derived essential oils ingredient having a fifth percentage (%) by weight, an excipients component having a sixth percentage (%) by weight, and water

202

Obtaining a plant-based extract complex composition by mixing in a specific order into a container including the ginseng extract solution, the medicinal herb extract solution, the plant-derived nanovesicles ingredient, the methyl salicylate component, the plant-derived essential oils ingredient, the excipients component, and water to create a mixture; wherein after each addition of the mixing ingredients to the mixture is stirred until the mixture is homogeneous

203

Filling and packaging

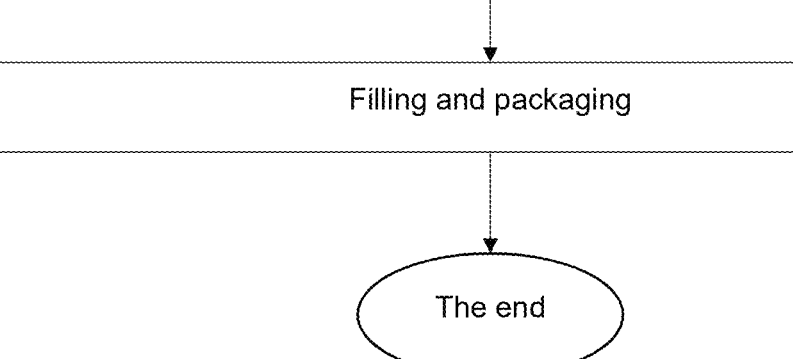

The end

PLANT-BASED EXTRACT COMPLEX COMPOSITION HAVING THE PROPERTIES FOR SUPPORTING THE RELIEF OF MUSCULOSKELETAL PAIN, ANTIBACTERIAL AND ANTI-INFLAMMATORY AND PROCESS OF MANUFACTURING THE SAME

FIELD OF THE INVENTION

The invention pertains to the field of health care product manufacturing, particularly to a plant-based extract complex composition effective in reducing symptoms the relief of musculoskeletal pain, supporting treatment of respiratory diseases. More specifically, the invention relates to a method for producing a plant-based extract complex composition having the properties for supporting the relief of musculoskeletal pain, antibacterial and anti-inflammatory and process of manufacturing the same.

BACKGROUND ART

Natural compounds are extracted from various sources, among which herbs are the most common. Due to their biodiversity, crude extracts from herbs often contain bioactive compounds such as tannins, flavonoids, alkaloids, and phenolics, which have been widely used as sources of natural medicines and health care products. In recent years, medicinal plants have attracted significant attention as a source of secondary metabolites for screening in the treatment of chemotherapeutic drug resistance, using in vitro, in vivo, and in silico approaches. Drug development through phytopharmaceutical techniques offers an efficient, cost-effective, and safe alternative to conventional methods such as animal cell culture and microbial fermentation. Therefore, plant-derived natural compounds have the potential to provide patients with faster and more accessible therapeutic options.

Extraction is the preliminary step to separate the desired natural products from the raw material. Different extraction methods are used based on the components and compounds in the plant extract. Distillation, sublimation, and solvent extraction are the most common methods used to extract the different active ingredients in plants. Some techniques with unique special mechanisms are created to ensure better extraction efficiency. Ultrasonic extraction, microwave extraction, supercritical fluid extraction, and combined extraction with the help of ultrasound waves are advanced extraction techniques.

Nanovesicles derived from natural products are gaining attention as innovative therapeutic agents due to their biocompatibility, low immunogenicity, and ability to transport bioactive molecules such as proteins, lipids, and nucleic acids. Plant-derived nanovesicles exhibit structural similarities to mammalian exosomes, making them suitable for drug delivery, microbiome-targeted therapy, and regenerative medicine. Nanovesicles' Potential applications include treating cancer, inflammation, and metabolic disorders. Additionally, nanovesicles have applications in cosmetics, agriculture, and the food industry.

Inflammation is the body's defense response to harmful stimuli such as allergens and/or tissue damage; on the other hand, the uncontrolled inflammatory response is the main cause of a variety of disorders, including allergies, cardiovascular dysfunction, metabolic syndrome, cancer, and autoimmune diseases that impose a huge economic burden on individuals and therefore on society. There are many different drugs to control and prevent inflammation. However, some drugs will cause side effects; the goal is to use effective doses with the least side effects. Therefore, it is necessary to apply anti-inflammatory factors from natural extracts to enhance pharmacological effects and reduce the level of unwanted side effects to the lowest level.

It can be seen that the above technical solutions all meet the set purposes and requirements. However, the above inventions are still limited in that the compound components are very volatile, easily oxidized, and evaporated within a few hours, as well as the ability to penetrate the capillaries under the skin to help reduce pain, muscle stiffness due to heavy activities or sports, especially effective in physical therapy support. In addition, these preparations need to be controlled for the ability to cause skin irritation, not poisoning and odor for users when they are in working outdoors for a long time.

Therefore, it is necessary to provide a plant-based extract complex composition containing stable, non-volatile, easy-to-use, and multifunctional active ingredients, which can be used as a massage medicine to support the relief of joint pain and inflammation, as well as antibacterial and antiviral products used externally on the skin or through the nose such as herbal inhalation products.

It is also necessary to provide a plant-based extract complex composition having the relief of musculoskeletal pain, antibacterial and anti-inflammatory does not cause any negative effects on the user's health and does not cause skin irritation.

Finally, it is also necessary to provide a plant-based extract complex composition having affordable and easy to produce, taking advantage of available raw materials, easy to collect, non-toxic, environmentally friendly but still ensuring the quality and effectiveness of the relief of musculoskeletal pain, antibacterial and anti-inflammatory.

This invention provides solutions to achieve the above goals.

SUMMARY OF THE INVENTION

Accordingly, the first aspect of the invention is to provide a plant-based extract complex composition having the properties for supporting the relief of musculoskeletal pain, antibacterial and anti-inflammatory is obtained from the process of forming a homogeneous mixture by mixing in a specific order into a container including (A) a ginseng extract solution having a first percentage (%) by weight, (B) a medicinal herbs extract solution having a second percentage (%) by weight, (C) a plant-derived nanovesicles ingredient having a third percentage (%) by weight, (D) a plant-derived essential oils ingredient having a fourth fifth percentage (%) by weight, (E) a methyl salicylate component having a fifth percentage (%) by weight, (F) an excipients component having a sixth percentage (%) by weight, and (G) water to create a mixture; wherein after each addition of the mixing ingredients to the mixture is stirred until the mixture is homogeneous; wherein after each addition of the mixing component to the container, the complex is stirred until complex is homogeneous; wherein the percentage (%) by weight is determined by the sum from the first percentage (%) to the sixth percentage (%) plus the percentage (%) of the water to make up 100%.

The second aspect of the invention is to provide a plant-based extract complex composition having the properties for supporting the relief of musculoskeletal pain, antibacterial and anti-inflammatory depend on the percentage (%) by weight of each ingredients (A)-(G) including a first formula, a second formula, a third formula, and a fourth formula; wherein the third formula is stronger than the first formula, the first formula is stronger than the second formula, and the second formula is stronger than the fourth formula; in which the comparative factor is properties for supporting the relief of musculoskeletal pain, antibacterial and anti-inflammatory. These four formulas can be used as massage balm, massage gel, inhalation oil, liniment oil, aromatherapy products, medicinal products such as pain relief, expectorant products, and skin care products, etc.

The third aspect of the invention is to provide a plant-based extract complex composition having the properties for supporting the relief of musculoskeletal pain, antibacterial and anti-inflammatory according to the first formula comprises: (A) the ginseng extract solution having 0.01%-0.5% by weight; (B) the medicinal herbs extract solution having 12%-55% by weight; (C) the plant-derived nanovesicles ingredient having 5%-10% by weight; (D) the plant-derived essential oils ingredient having 10%-28% by weight; (E) the methyl salicylate component having 0.001%-0.8% by weight; (F) the excipient component having 0.001%-5% by weight; and (G) the remainder is the water.

The fourth aspect of the invention is to provide a plant-based extract complex composition having the properties for supporting the relief of musculoskeletal pain, antibacterial and anti-inflammatory according to the second formula comprises: (A) the ginseng extract solution having 0.01%-0.5% by weight; (B) the medicinal herbs extract solution having 0.1%-12% by weight; (C) the plant-derived nanovesicles ingredient having 1%-5% by weight; (D) the plant-derived essential oils ingredient having 28%-48% by weight; (E) the methyl salicylate component having 0.8%-10% by weight; (F) the excipient component having 0.001%-5% by weight; and (G) the remainder is the water.

Another objective of the present invention is to provide a plant-based extract complex composition having the properties for supporting the relief of musculoskeletal pain, antibacterial and anti-inflammatory according to the third formula comprises: (A) the ginseng extract solution having 0.01%-0.5% by weight; (B) the medicinal herbs extract solution having 12%-55% by weight; (C) the plant-derived nanovesicles ingredient having 5%-10% by weight; (D) the plant-derived essential oils ingredient having 28%-48% by weight; (E) the methyl salicylate component having 0.8%-10% by weight; (F) the excipient component having 0.001%-5% by weight; and (G) the remainder is the water.

Another objective of the present invention is to provide a plant-based extract complex composition having the properties for supporting the relief of musculoskeletal pain, antibacterial and anti-inflammatory according to the fourth formula comprises: (A) the ginseng extract solution having 0.01%-0.5% by weight; (B) the medicinal herbs extract solution having 0.1%-12% by weight; (C) the plant-derived nanovesicles ingredient having 1%-5% by weight; (D) the plant-derived essential oils ingredient having 28%-48% by weight; (E) the methyl salicylate component having 0.001%-0.8% by weight; (F) the excipient component having 0.001%-5% by weight; and (G) the remainder is the water.

Another objective of the present invention is to provide a process of manufacturing a plant-based extract complex composition having the properties for supporting the relief of musculoskeletal pain, antibacterial and anti-inflammatory comprising:

(i) preparing material including: (A) a ginseng extract solution having a first percentage (%) by weight, (B) a medicinal herbs extract solution having a second percentage (%) by weight, (C) a plant-derived nanovesicles ingredient having a third percentage (%) by weight, (D) a plant-derived essential oils ingredient having a fourth percentage (%) by weight, (E) a methyl salicylate component having a fifth percentage (%) by weight, (F) an excipients component having a sixth percentage (%) by weight, and (G) water;

(ii) obtaining a plant-based extract complex composition by mixing in a specific order into a container including (A) a ginseng extract solution having a first percentage (%) by weight, (B) a medicinal herbs extract solution having a second percentage (%) by weight, (C) a plant-derived nanovesicles ingredient having a third percentage (%) by weight, (D) a plant-derived essential oils ingredient having a fourth percentage (%) by weight, (E) a methyl salicylate component having a fifth percentage (%) by weight, (F) an excipients component having a sixth percentage (%) by weight, and (G) water to create a mixture;

wherein after each addition of the mixing ingredients to the mixture is stirred until the mixture is homogeneous; and wherein the percentage (%) by weight is determined by the sum from the first percentage (%) to the sixth percentage (%) plus the percentage (%) of the water to make up 100%; and (iii) filling and packaging.

Finally, another objective of the present invention is to provide a method for supporting the relief of musculoskeletal pain, antibacterial and anti-inflammatory comprising topically applying a plant-based extract complex composition to the skin at the pain location of a subject in need thereof, wherein the plant-based extract complex composition is obtained from the process of forming a homogeneous mixture by mixing in a specific order into a container including (A) a ginseng extract solution having a first percentage (%) by weight, (B) a medicinal herbs extract solution having a second percentage (%) by weight, (C) a plant-derived nanovesicles ingredient having a third percentage (%) by weight, (D) a plant-derived essential oils ingredient having a fifth percentage (%) by weight, (E) a methyl salicylate component having a fourth percentage (%) by weight, (F) an excipients component having a sixth percentage (%) by weight, and (G) water to create a mixture; wherein after each addition of the mixing ingredients to the mixture is stirred until the mixture is homogeneous; wherein the percentage (%) by weight is determined by the sum from the first percentage (%) to the sixth percentage (%) plus the percentage (%) of the water to make up 100%.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

FIG. 1 is a flowchart illustrating a process of manufacturing plant-based extract complex composition having the properties for supporting the relief of musculoskeletal pain, antibacterial and anti-inflammatory in accordance with an embodiment of the present invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skills in the art that the present invention may be practiced without these specific details. In other instances, well-known methods, procedures, components, and circuits have not been described in detail so as not to unnecessarily obscure aspects of the present invention.

In the embodiment of the present invention, percent mass or percentage (%) by weight=(mass of solute/mass of solution)×100%. The unit of mass is usually grams, or kilograms. Mass percent is also known as the correct percentage by weight or w/w %. It should also be noted that the molar mass is also within the meaning of the invention. Molar mass is the total mass of all atoms in a mole of compound. Total all volume percentages add up to 100%.

According to the embodiment of the invention, a plant-based extract complex composition having the properties for supporting the relief of musculoskeletal pain, antibacterial and anti-inflammatory 100 ("composition 100") is obtained from the process of forming a homogeneous mixture by mixing in a specific order into a container including the mixing ingredients Z1 to Z7 are listed in Tables 1 below: a ginseng extract solution having a first percentage (%) by weight, a medicinal herbs extract solution having a second percentage (%) by weight, a plant-derived nanovesicles ingredient having a third percentage (%) by weight, a plant-derived essential oils ingredient having a fourth percentage (%) by weight, a methyl salicylate component having a fifth percentage (%) by weight, an excipients component having a sixth percentage (%) by weight, and water to create a mixture; wherein after each addition of the mixing ingredients to the mixture is stirred until the mixture is homogeneous; wherein the percentage (%) by weight is determined by the sum from the first percentage (%) to the sixth percentage (%) plus the percentage (%) of the water to make up 100%. It should be noted that the mixing ingredients Z1 to Z7 are not mixed in the specific order described, the final product will not support the relief of musculoskeletal pain, antibacterial and anti-inflammatory. Within the scope of the present invention, the term "homogeneous mixture" includes the following meanings:

(a) A homogeneous mixture is a solution that completely dissolves in a specific order the ingredients (Z1) to (Z7) having the correct percentage (%) by weight;

(b) A homogeneous mixture acts as a reactant, allowing the addition of ingredients to contribute their chemical and physical properties to create a new composition; and (c) A homogeneous mixture chemically bonds with other complementary ingredients including but not limited to ionization reactions, covalent reactions, reducing reactions, replacement reactions, and rearrangement reactions to form a new chemical composition.

According to the embodiment of the invention, the properties for supporting the relief of musculoskeletal pain, antibacterial and anti-inflammatory depend on the percentage (%) by weight of each ingredient Z1-Z7 including a first formula, a second formula, a third formula, and a fourth formula; wherein the third formula is stronger than the first formula, the first formula is stronger than the second formula, and the second formula is stronger than the fourth formula; in which the comparative factor is properties for supporting the relief of musculoskeletal pain, antibacterial and anti-inflammatory.

TABLE 1

The mixing ingredients Z1 to Z7 to create the composition 100 according to the embodiment of the invention

| | | Percentage (%) by weight | | | |
|---|---|---|---|---|---|
| Note | The ingredient | first formula | second formula | third formula | fourth formula |
| Z1 | The ginseng extract solution | 0.01-0.5 | 0.01-0.5 | 0.01-0.5 | 0.01-0.5 |
| Z2 | The medicinal herbs extract solution | 12-55 | 0.1-12 | 12-55 | 0.1-12 |
| Z3 | The plant-derived nanovesicles ingredient | 5-10 | 1-5 | 5-10 | 1-5 |
| Z4 | The plant-derived essential oils ingredient | 10-28 | 28-48 | 28-48 | 28-48 |
| Z5 | The methyl salicylate component | 0.001-0.8 | 0.8-10 | 0.8-10 | 0.001-0.8 |
| Z6 | The excipients component | 0.001-5 | 0.001-5 | 0.001-5 | 0.001-5 |
| Z7 | The water | rest | rest | rest | rest |

7

8

Next, referring to FIG. 1, a process 200 for manufacturing a composition 100 in accordance to an exemplary embodiment of the present invention is illustrated.

At step 201, all ingredients Z1 to Z7 are carefully prepared and stored in separate containers.

According to the embodiment of the invention, the ginseng extract solution (Z1) is extracted from parts of ginseng, including roots, stems, leaves, and flowers that have been cleaned, then crushed or chopped and soaked in solvent or saline solution. According to the preferred embodiment of the present invention, the roots have a minimum age of 5 years old; stems, leaves, and flowers of ginseng have a minimum age of 3 years old. The ginseng parts are selected from one or more parts in the genus *Panax* of the including *Panax notoginseng, Panax bipinnatifidus, Korean ginseng, Panax japonicus, American ginseng, Panax quonquefolius, Panax vietnamensis, Panax wangianus, Panax zingiberebsis, Panax pseudoginseing,* and *Panax stipuleanatus.*

According to the embodiment of the invention, the medicinal herbs extract solution (Z2) is prepared by performing steps (a1) to (a3):

(a1) collecting and pre-processing material from medicine herbals (a)-(l) are listed in Tables 2 below including removing damaged parts, washing, and drying to 8%-15% moisture, chopping and stored in separate instruments;

(a2) creating a medicine herbals mixture by performing steps (a') to (b'):

(a') collecting and pre-processing material from medicine herbals (m)-(n) are listed in Tables 2 below, including removing damaged parts, washing, drying overnight exposed to dew and drying to 8%-15% moisture, chopping and stored in separate instruments; wherein the material from medicine herbals (m)-(n) include: (m) *Salvia miltiorrhiza*, and (n) *Achyranthes bidentate* uses the roots; and (b') mixing the material from medicine herbals (a)-(l) prepared in step (a1) and the material from medicine herbals (i)-(n) prepared in step (a') to obtain the medicine herbals mixture; and (a3) soaking the medicine herbals mixture with 70% ethanol solvent in a ratio of 18:70 w/v at room temperature, stirring at a frequency of 200-250 rpm for 10 days to obtain a mixture 1, filtering the mixture 1 to obtain a filtrate 1 and residue 1; soaking the residue 1 with 70% ethanol solvent in a ratio of 18:70 w/v, stirring at a frequency of 200-250 rpm for 10 days to obtain a mixture 2, filtering the mixture 2 to obtain a filtrate 2 and residue 2; soaking the residue 2 with 70% ethanol solvent in a ratio of 18:70 w/v, stirring at a frequency of 200-250 rpm for 10 days to obtain a mixture 3, filtering the mixture 3 to obtain a filtrate 3 and a residue 3; mixing the filtrate 1 with the filtrate 2, and filtrate 3 to obtain a filtrate mixture, removing the solvent from the filtrate mixture by vacuum evaporation at 40° C.-45° C. to obtain the medicinal herbs extract solution.

TABLE 2

The medicinal herbs ingredients (a)-(l) to create the medicinal herbs extract solution according to the embodiment of the invention

| Note | Name of | Scientific name | Part used | Compound | Indications | Distribution |
|------|---------|-----------------|-----------|----------|-------------|--------------|
| (a) | The safflower | *Carhamus tinctorius* L | flower | Carthamin Hydroxysafflor Flavonoid (Kaempferol) | Activating blood circulation | Ha Giang, Northern midland and mountainous region of Vietnam |
| (b) | The Dragon's Blood | *Daemonorops draco* (Willd.) Blume | The resin from the fruit and stem | Dracoresin Acid benzoic Essential oil | Activating blood circulation | Indonexia |
| (c) | The Chinese goldthread | *Coptis chinensis* Franch. | The roots and tubers | Berberin | Antibacterial and anti-inflammatory | Lao Cai (Sapa), Hoang Lien Son mountain range, Northwestern region of Vietnam |
| (d) | The Japanese knotweed | *Reynoutria japonica* Houtt. | The roots and tubers | Anthraglycosid Polydatin, resveratrol | Musculoskeletal pain | Lao Cai, Yen Bai, Son La, Dien Bien, and Hoa Binh provinces |
| (e) | The cinnamon | *Cinnamomum loureiroi* Nees | The bark | Cinnamaldehyde Coumarin | Musculoskeletal pain | Cao Bang, Yen Bai, Quang Ninh, Thanh Hoa, Nghe An, and Thai Nguyen provinces |

TABLE 2-continued

The medicinal herbs ingredients (a)-(l) to create the medicinal herbs
extract solution according to the embodiment of the invention

| Note | Name of | Scientific name | Part used | Compound | Indications | Distribution |
|------|---------|-----------------|-----------|----------|-------------|--------------|
| (f) | The ginger | *Zingiber officinale* Rosc. | The tubers | Gingerol Shogaol Zingerone | Cold hands and feet, Painful numbness and weakness, Arthralgia syndrome | In Vietnam, ginger is cultivated across all provinces nationwide, from mountainous regions to the plains |
| (g) | The star anise | *Illicium verum* Hook. f. | the fruits | Anethole | Painful numbness associated with Bi syndrome and arthritis | Cao Bang, Lang Son, Tuyen Quang, Bac Kan, Ha Giang, and Thai Nguyen provinces |
| (h) | The piper lolot | *Piper sarmentosum* | all parts of the plant | Beta-caryophyllene Benzyl acetate alkaloid: piperine, piperidine, piplartine flavonoid: quercetin, kaempferol, apigenin | Treatment of disorders caused by wind, cold, and dampness, leading to numbness and paralysis of the hands and feet | The plains and midland regions of Vietnam |
| (i) | The mugwort | *Artemisia vulgar* | the leaves | Essential oil: Monoterpen, Sesquiterpen lacton, và Este dehydromatricaria Flavonoid | Pain relief for musculoskeletal pain, sciatica, and arthritis; Supporting cerebral blood circulation | Northern mountainous provinces such as Lao Cai, Lai Chau, Yen Bai Cao Bang, Lang Son, and Ha Giang |
| (j) | The codonopsis | *Codonopsis pilosula* Nannf | the tubers | Saponin Polysaccharide | Enhancing red blood cell production, promoting blood nourishment, and improving anemia conditions | Lam Dong, Quang Nam, Kon Tum, Da Nang, Ha Giang, Lang Son, Lai Chau, Lao Cai, and Cao Bang provinces |
| (k) | The clove | *Flos caryophylatac* | flower bud | Eugenol beta-caryophyllene | Musculoskeletal pain | The Moluccas Islands region of Indonesia, Asia, and Africa |
| (l) | The white mustard seed | *Brassica alba* | seeds | Myrosin, sinapine, sinalbin, sinigrin, fatty oils, saponins | Anti-inflammatory, reduces swelling, treats musculoskeletal pain | Vietnam |
| (m) | The Dan Shen | *Salvia miltiorrhiza* | the roots | Danshensu (3-(3,4-dihydroxyphenyl) lactic acid) | Antithrombotic | China |
| (n) | The goat's head | *Achyranthes bidentata* | the roots | Saponin triterpenoid | Treatment of arthritis and lower back pain | China |

According to the embodiment of the invention, the plant-derived nanovesicles ingredient (Z3) is prepared by mixing a first nanovesicles ingredient with a second nanovesicles ingredient in a ratio of 2:3 w/w.

According to the embodiment of the invention, the first nanovesicles ingredient is prepared by performing steps (b1) to (b8):

(b1) collecting the material from plants in the following percentage (%) by weight including 2 parts of *Illicium verum* Hook. f., 3 parts of *Artemisia vulgaris*, and 3 parts of *Piper sarmentosum* to obtain a temporary mixture;

(b2) washing the temporary mixture three times with deionized water at 20° C.-25° C.;

(b3) pureeing the washed temporary mixture with phosphate buffer solution (PBS) in a ratio of 1:3 w/v at a speed of 7,000-8,000 rpm for 15 minutes to obtain a first temporary solution;

(b4) filtering the first temporary solution by a filter membrane with a diameter 0.20-0.22 μm to obtain a second temporary solution;

(b5) centrifuging the second temporary solution by ultra-centrifugation at 120,000×g for 100 min at 4° C. to obtain a temporary residue;

(b6) dissolving the temporary residue in phosphate buffer solution (PBS), transferring to a 45% sucrose gradient solution, and ultracentrifuging at 130,000×g for 100 min to obtain a third temporary solution;

(b7) washing the third temporary solution with PBS and centrifuging at 150.000×g for 60 min at 4° C. to obtain a fourth temporary solution; and (b8) filtering the fourth temporary solution through a filter membrane with a diameter 0.20-0.22 μm to obtain the first nanovesicles ingredient.

According to the embodiment of the invention, the second nanovesicles ingredient is prepared by performing steps (c1) to (c9):

(c1) collecting a fruit mixture in the following percentage (%) by weight including 3 parts of dragon fruit (*Hylocereus undatus, Hylocereus costaricensis, Hylocereus megalanthus, Hylocereus undatus costaricensis*), 3 parts of avocado (*Persea americana*), and 1 part of watermelon (*Citrullus lanatus*);

(c2) washing the fruit mixture three times with deionized water at 20° C.-25° C.;

(c3) pureeing the washed fruit mixture with phosphate buffer solution (PBS) in a ratio of 1:1 (g/mL) at a speed of 7,000-8,000 rpm for 15 minutes to obtain a first foundation solution;

(c4) filtering the first foundation solution by a filter membrane with a diameter 0.20-0.22 μm to obtain a second foundation solution;

(c5) centrifuging the second foundation solution by ultra-centrifugation at 100,000×g for 60 min to obtain a residue;

(c6) dissolving the residue in phosphate buffer solution (PBS), transferring to a 45% sucrose gradient solution, and ultracentrifuging at 130,000×g for 100 min to obtain a third foundation solution;

(c7) stirring the third foundation solution with a 10% polyethylene glycol-8000 (PEG8000) solution in a ratio of 1:1 v/v, and incubating for 8-10 hours at 4° C., then centrifuging at 110,000×g for 40 minutes at 4° C. to obtain a precipitate;

(c8) dissolving the precipitate in phosphate buffer solution (PBS) in a ratio of 1:2 w/v to obtain a foundation solution; and (c9) filtering the foundation solution by a tangential flow filtration (TFF) to obtain the second nanovesicles ingredient; wherein the technical specifications related to TFF include a molecular size of 500 kDa, and filtering at a flow rate of 20 mL/min with the transmembrane pressure maintained at 2 bar.

According to the embodiment of the invention, the plant-derived essential oils ingredient (Z4) is prepared by mixing in the following percentage (%) by weight including the essential oils ingredients (a')-(h') are listed in Tables 3 below, including: 1-2 parts of an essential oil of cajeput leaf, 2 parts of an essential oil of camphor leaf, 1 part of an essential oil of cinnamon leaf, 1-2 parts of an essential oil of *eucalyptus* leaf, 2 parts of an essential oil of rosemary leaf, 1 part of an essential oil of peppermint leaf, 1-2 parts of an essential oil of *perilla* seed, and 1 part of an essential oil of ginger rhizome;

TABLE 3

| | | | | | |
|---|---|---|---|---|---|
| The plants selected as raw materials to create the plant-derived essential oils ingredient (Z4) according to the embodiment of the invention | | | | | |
| Note | Name of | Scientific name | Part used | Indications | Distribution |
| (a') | The essential oil of cajeput leaf | *Melaleuca cajuputi* | leaf | Supporting the treatment of respiratory diseases and enhancing the immune system | Thua Thien Hue, Quang Binh, Quang Tri, Long An, Dong Thap, and Tay Ninh provinces |
| (b') | The essential oil of camphor leaf | *Cinnamomum camphora* | leaf | Analgesic, anti-inflammatory, antibacterial, and respiratory-supporting effects | Ha Giang, Tuyen Quang, Phu Tho, Cao Bang, and Lang Son provinces |
| (c') | The essential oil of cinnamon leaf | *Cinnamomum verum* | leaf | Antibacterial, anti-inflammatory, and stress-relieving effects | Thanh Hoa, Nghe An, Khanh Hoa, Tay Ninh, Ba Ria-Vung Tau, and Kien Giang (Phu Quoc) provinces |
| (d') | The essential oil of eucalyptus leaf | *Eucalyptus globulus* Labill. | leaf | Supporting respiratory health, relieving stress, and enhancing immunity | Central Vietnam and the Central Highlands |

TABLE 3-continued

The plants selected as raw materials to create the plant-derived essential oils
ingredient (Z4) according to the embodiment of the invention

| Note | Name of | Scientific name | Part used | Indications | Distribution |
|------|---------|-----------------|-----------|-------------|--------------|
| (e') | The essential oil of rosemary leaf | *Salvia rosmarinus* | leaf | Enhancing memory, relieving stress, supporting the respiratory system, improving oral health, promoting skin care, and stimulating hair growth | Central Vietnam and Southern Vietnam |
| (f') | The essential oil of peppermint leaf | *Mentha arvensis* L | leaf | Supporting digestion, relieving pain, cooling the body, and promoting relaxation | Lao Cai, Nghe An, Lai Chau, Yen Bai provinces |
| (g') | The essential oil of perilla seed | *Perilla frutescens* (L.) Britt. | seed | Anti-allergic, anti-inflammatory, anti-cancer, stress-relieving, weight management-supporting, and skin-improving effects | Vietnam |
| (h') | The essential oil of ginger rhizome | *Zingiber officinale* Rosc. | rhizome | Supporting digestion, relieving nausea and pain, exhibiting anti-inflammatory effects, and promoting blood circulation | In Vietnam, ginger is cultivated across all provinces nationwide, from mountainous regions to the plains |

According to the preferred embodiment of the present invention, each essential oils ingredient (a')-(h') is extracted by performing steps (d1) to (d3):

(d1) collecting and pre-processing material from plant individually including removing damaged parts, washing, chopping, and soaking with an enzyme solution in a ratio of 1:2 w/v for 30 minutes, and filtering to obtain an enzyme-treated plant material;

in which the enzyme solution is prepared by:

creating an enzyme composition by mixing a cellulase with hemicellulase, and xylanase in a ratio of 1:1:1 w/w/w; and dissolving the enzyme composition with water in a ratio of 1:15000 w/v;

(d2) grinding a mixture of 1 part the enzyme-treated plant material with 7 parts saturated salt solution, let stand after grinding for 1 hour with microwave assistance at a power of 300-500 W, then steam distillation for 3 hours to obtain a crude essential oil; and (d3) removing water from the crude essential oil by adding $Na_2SO_4$ salt to crystallize at $-15°$ C., and filtering to obtain the plant-derived essential oils ingredient.

According to the embodiment of the invention, the methyl salicylate component (Z5) is synthesized by:

dissolving 1.5 g of salicylic acid (10 mmol) with 4.35 mL of 10% methanol in a 250 mL three-necked flask, adding 0.27 mL of 10% $H_2SO_4$, and refluxing at $82°$ C.-83° C. for 6 hours;

evaporating by rotary vacuum evaporation of the mixture after reaction at $62°$ C.-65° C. to remove the solvent, cooling the mixture after evaporation and putting it in a decanter;

coating the rotary vacuum evaporation flask with saturated $NaHCO_3$ solution put it in the decanter, adding 7 mL of saturated $NaHCO_3$ to the decanter, gently shaking the decanter then let it stand to obtain a lower solution layer;

washing the lower solution layer three times with saturated $NaHCO_3$ solution, wherein each time washing with saturated $NaHCO_3$ solution is 7 mL;

washing the lower solution layer three times with distilled water, wherein each time washing with distilled water is 12 mL; and adding 0.5 g of anhydrous $Na_2SO_4$ into the reaction mixture, filtering, and distilling fractional to obtain the methyl salicylate component at temperature of 220° C.

According to the embodiment of the invention, the excipients component (Z6) is selected from the group consisting of ethanol, polysorbate 60, sorbitan oleate, triethanolamine, carbomer or combinations thereof. These molecules can be used in native form or with chemical modifications. Such components may be used individually or in combination.

Still with FIG. 1, at step 102, obtaining a plant-based extract complex composition by mixing in a specific order into a container the ingredients (Z1)-(Z7) including: a ginseng extract solution having a first percentage (%) by weight, a medicinal herbs extract solution having a second percentage (%) by weight, a plant-derived nanovesicles ingredient having a third percentage (%) by weight, a plant-derived essential oils ingredient having a fourth percentage (%) by weight, a methyl salicylate component having a fifth percentage (%) by weight, an excipients component having a sixth percentage (%) by weight, and (G) water to create a mixture;

wherein after each addition of the mixing ingredients to the mixture is stirred until the mixture is homogeneous; and wherein the percentage (%) by weight is determined by the sum from the first percentage (%) to the sixth percentage (%) and plus the percentage (%) of solvent is the water to make up 100%.

It is also noted that the terminology "admixed" in step 202 used in the present invention means that foundation mixture is added or reacted with or dissolved homogeneously to the plurality of mixing ingredients (Z1-Z7) using stirrers such as magnetic stirrers. Step 202 is performed by a magnetic stirrer. Magnetic stirrer has been known in previous art so the description of the structure and its operating principle will not be described in detail in the invention.

According to the embodiment of the invention, the properties for supporting the relief of musculoskeletal pain, antibacterial and anti-inflammatory depend on the percentage (%) by weight of each ingredients (Z1)-(Z7) mixed in step 202, the composition 100 is obtained from the process 200 including a first formula, a second formula, a third formula, and a fourth formula are listed in Tables 1; wherein the third formula is stronger than the first formula, the first formula is stronger than the second formula, and the second formula is stronger than the fourth formula; in which the comparative factor is properties for supporting the relief of musculoskeletal pain, antibacterial and anti-inflammatory.

According to the embodiment of the invention, the composition 100 according to the first formula comprises: (Z1) the ginseng extract solution having 0.01%-0.5% by weight; (Z2) the medicinal herbs extract solution having 12%-55% by weight; (Z3) the plant-derived nanovesicles ingredient having 5%-10% by weight; (Z4) the plant-derived essential oils ingredient having 10%-28% by weight; (Z5) the methyl salicylate component having 0.001%-0.8% by weight; (Z6) the excipient component having 0.001%-5% by weight; and (Z7) the remainder is the water.

According to the embodiment of the invention, the composition 100 according to the second formula comprises: (Z1) the ginseng extract solution having 0.01%-0.5% by weight; (Z2) the medicinal herbs extract solution having 0.1%-12% by weight; (Z3) the plant-derived nanovesicles ingredient having 1%-5% by weight; (Z4) the plant-derived essential oils ingredient having 28%-48% by weight; (Z5) the methyl salicylate component having 0.8%-10% by weight; (Z6) the excipient component having 0.001%-5% by weight; and (Z7) the remainder is the water.

According to the embodiment of the invention, the composition 100 according to the third formula comprises: (Z1) the ginseng extract solution having 0.01%-0.5% by weight;

(Z2) the medicinal herbs extract solution having 12%-55% by weight; (Z3) the plant-derived nanovesicles ingredient having 5%-10% by weight; (Z4) the plant-derived essential oils ingredient having 28%-48% by weight; (Z5) the methyl salicylate component having 0.8%-10% by weight; (Z6) the excipient component having 0.001%-5% by weight; and (Z7) the remainder is the water.

According to the embodiment of the invention, the composition 100 according to the fourth formula comprises: (Z1) the ginseng extract solution having 0.01%-0.5% by weight; (Z2) the medicinal herbs extract solution having 0.1%-12% by weight; (Z3) the plant-derived nanovesicles ingredient having 1%-5% by weight; (Z4) the plant-derived essential oils ingredient having 28%-48% by weight; (Z5) the methyl salicylate component having 0.001%-0.8% by weight; (Z6) the excipient component having 0.001%-5% by weight; and (Z7) the remainder is the water.

Finally, at step 203, filling and packaging the composition 100.

According to the embodiment of the invention, the composition 100 is obtained from the process 200 is not limited to the dosage form, it can be in the form of a solution, a cream, a paste, a gel, a foam, a solid, or a powder, depending on the dosage form thereof.

According to the embodiment of the invention, a method for supporting the relief of musculoskeletal pain, antibacterial and anti-inflammatory comprising topically applying the composition 100 to the skin at the pain location of the subject in need thereof, wherein the composition 100 is obtained from the process 200 has been described above.

EXAMPLES

The following experimental section is provided purely by way of illustration and is not intended to limit the scope of the invention as defined in the appended claims. In the following experimental section, reference is made to the appended drawings, wherein:

The example 1-4: modulation 100 g the composition 100 is created by process 200, including four examples listed in Table 4 below.

TABLE 4 components of the composition 100 according four examples in accordance with exemplary embodiment of the present invention.

| No. | Components | | Example 1 | Example 2 | Example 3 | Example 4 |
|---|---|---|---|---|---|---|
| | | | | Weight (g) | | |
| Z1 | The ginseng extract solution | | 0.1 | 0.1 | 0.1 | 0.1 |
| Z2 | The medicinal herbs extract solution | | 45 | 12 | 45 | 12 |
| Z3 | The plant-derived nanovesicles component | | 5 | 2 | 5 | 2 |
| Z4 | Plant-derived essential oils component | essential oil of cajeput leaf | 1 | 1 | 4 | 4 |
| | | essential oil of camphor leaf | 1 | 1 | 2 | 2 |
| | | essential oil of cinnamon leaf | 1 | 1 | 2 | 2 |
| | | essential oil of eucalyptus leaf | 1 | 1 | 4 | 4 |
| | | essential oil of rosemary leaf | 1 | 1 | 2 | 2 |
| | | essential oil of peppermint leaf | 1 | 1 | 2 | 2 |
| | | essential oil of perilla leaf | 1 | 1 | 4 | 4 |
| | | essential oil of ginger rhizome | 1 | 1 | 2 | 2 |
| Z5 | The methyl salicylate component | | 0.3 | 0.9 | 0.9 | 0.3 |
| Z6 | The excipients component | ethanol | 0.05 | 0.001 | 0.001 | 1.4 |
| | | polysorbate 60 | 0.001 | 1 | 1 | 0.9 |
| | | sorbitan oleate | 0.001 | 1 | 1 | 0.9 |
| | | triethanolamine | 0.001 | 1 | 1 | 0.2 |

TABLE 4-continued components of the composition 100 according four examples in accordance with exemplary embodiment of the present invention.

| No. | Components | Weight (g) | | | |
| | | Example 1 | Example 2 | Example 3 | Example 4 |
| --- | --- | --- | --- | --- | --- |
| | carbomer | 0.001 | 1 | 1 | 0.001 |
| Z7 | Water | rest | rest | rest | rest |

The composition 100 according to examples 1-4 is not limited to the dosage form, it can be in the form of a solution, a cream, a paste, a gel, a foam, a solid, or a powder. According to the preferred embodiment of the present invention, composition 100 according to examples 1-3 is used to support the symptoms of inflammation, bone, and joint pain; and composition 100 according to example 4 is preferably in liquid form for external use, nasal deconges- tant, respiratory support or steam inhalation or as an ingre- dient for relaxing massage.

The results of the analysis of the bactericidal and safety properties of the composition 100 according to examples 1-4 were tested for toxicity at a dose of 0.01 mL/20 body weight, applied to the back skin for 30 days in mice, showing no effect on the parameters of red blood cells, AST, ALT, and creatinine. The composition of 100 increased the number of leukocytes but did not affect the ratio of MID cells, mono- cytes, and granulocytes compared to the control group using a solvent. At the same time, there was no difference in the microstructural characteristics of the liver and kidney of mice after using preparation 100 compared to the control group using solvent.

The composition 100, according to examples 1-4, was tested for biological activity including an antioxidant test by DPPH free radical scavenging and anti-lipid peroxidation ability, and antibacterial activity tests listed in Table 5 below.

TABLE 5

Results of biological activity testing of the composition 100 according to the embodiment of the present invention

| No. | Biological activity testing | The results |
| --- | --- | --- |
| 1 | The DPPH free radical scavenging | (+) |
| 2 | The anti-lipid peroxidation ability | (+) |
| 3 | The antibacterial activity | Staphylococcus aureus, Escherichia coli, Candida albicans, Pseudomona saeruginosa, Bacillus subtilis | wherein (+) is a positive sample; it has DPPH free radical scavenging and anti-lipid peroxidation ability greater than 50%.

The example 5 evaluating the skin irritation of the com- position 100, which is obtained from the example 3 in accordance with an exemplary embodiment of the present invention.

Test subjects: the experiment was performed on New Zealand White, white fur. Rabbits met the experimental requirements: healthy adult (9-10 weeks old), regardless of gender, healthy skin and no skin diseases. Total of 03 rabbits was used for experimental (weight: 2.0-2.2 kg/rabbit). Rab- bits were kept separately to avoid possible cross-infection through the respiratory tract and contact; They were accli- matized raised in experimental conditions for 5 days prior to the research; room temperature 25° C.-30° C., light guaran- teed 12 hours of darkness, 12 hours of light every day. Rabbits were fed according to the food standards for research animals, water (boiled and cooled) drink freely. total of 03 rabbits was used for experimental Animal preparation: 24 hours before the experiment, rabbits were shaved to remove the fur in the back and hips. Divide the shaved skin into two sections, choosing each section to be about 6 cm² (2.5 cm×2.5 cm).

Experimental design: Conduct a drug test with 3 rabbits; each rabbit is used to apply 0.5 g of the composition 100, and the skin without drug application is used as a control. Prepare non-irritating gauze with dimensions of 2.5 cm×2.5 cm. Place the composition 100 on the gauze, with a dose of 0.5 g, spread evenly over the surface of the gauze. Place the gauze on the rabbit skin (1 gauze/rabbit). Fix the gauze with non-irritating adhesive tape. Mark the location of the test sample with a marker. After 4 hours of fixing the gauze on the rabbit skin, remove the gauze and tape and clean with distilled water. Observe, evaluate, and score the erythema and oedema indices on the skin where the composition 100 was applied compared to the adjacent skin where the com- position 100 was not applied was described and scored according to the scoring system in Table 6 at 1 hour, 24 hours, 48 hours, and 72 hours after cleaning the composition 100. If there is any damage, monitor the rabbit for 14 days to assess the recovery ability. When the damage has recov- ered, stop monitoring.

TABLE 6

Scoring of erythema and oedema

| Reaction | Rating Points |
| --- | --- |
| erythema | |
| No erythema | 0 |
| Very slight erythema (barely perceptible) | 1 |
| Well defined erythema | 2 |
| Moderate to severe erythema | 3 |
| Severe erythema | 4 |
| oedema | |
| No oedema | 0 |
| Very slight oedema (barely perceptible) | 1 |
| Well defined oedema (edges of area raised) | 2 |
| Moderate to severe oedema (edges of area raised~1 mm) | 3 |
| Severe oedema (edges of area raised more than 1 mm and extending outside the application area) | 4 |

Evaluation of results: For each rabbit, the irritation score was calculated by dividing the sum of the two levels of erythema and edema by the number of observations. The irritation score of the composition 100 is taken as the average of the irritation score of the tested rabbits. The irritation score is compared with the levels prescribed in Table 7 to determine the skin irritation potential of the test sample on rabbits.

TABLE 7

| Classification of skin irritation levels on rabbits | |
| --- | --- |
| Irritation category | Mean score |
| Negligible Irritation | 0-0.5 |
| Slight Irritation | >0.5-2.0 |
| Moderate Irritation | >2.0-5.0 |
| Severe Irritation | >5.0-8.0 |

The Result

TABLE 8

| | Skin irritation level of the composition 100 on rabbit skin | | | | | | | | | | | | | | | |
| --- | --- | --- | --- | --- | --- | --- | --- | --- | --- | --- | --- | --- | --- | --- | --- | --- |
| | Time | | | | | | | | | | | | | | | |
| | 1 hour | | | | 24 hours | | | | 48 hours | | | | 72 hours | | | |
| | erythema | | oedema | | erythema | | oedema | | erythema | | oedema | | erythema | | oedema | |
| Rabbit | CP | ĐC | CP | ĐC | CP | ĐC | CP | ĐC | CP | ĐC | CP | ĐC | CP | ĐC | CP | ĐC |
| 1 | 1 | 0 | 1 | 0 | 1 | 0 | 1 | 0 | 0 | 0 | 0 | 0 | 0 | 0 | 0 | 0 |
| 2 | 0 | 0 | 0 | 0 | 0 | 0 | 0 | 0 | 0 | 0 | 0 | 0 | 0 | 0 | 0 | 0 |
| 3 | 0 | 0 | 0 | 0 | 0 | 0 | 0 | 0 | 0 | 0 | 0 | 0 | 0 | 0 | 0 | 0 |
| Mean | 0.3 | 0 | 0.3 | 0 | 0.3 | 0 | 0.3 | 0 | 0 | 0 | 0 | 0 | 0 | 0 | 0 | 0 |

Note:
CP: applied area the composition 100; ĐC: Control area

Based on Table 8 shows that: at 1 hour after removing the composition 100, the total irritation score was 0.3+0.3=0.6, classified as slight irritation. At 24 hours: The total irritation score was 0.6, classified as slight irritation. At 48 hours: The total irritation score was 0.0, classified as negligible irritation. At 72 hours: The total irritation score was 0.0, classified as negligible irritation. The skin used as a control showed that at all time points, there were no signs of irritation.

At the time of the experiments, all rabbits were healthy, had normal function, and showed no signs of itchy rash or scratching at the site where the medicated gauze was placed. Rabbits ate, drank, lived, slept, etc. normally. There were no digestive disorders (such as diarrhea, increased salivation, etc.) or disorders of animal activities and motor behavior (tremors, convulsions, sleep disorders, coma). Compared with the classification of irritation levels on rabbit skin: The composition 100 of the preparation was classified as insignificantly irritating.

The example 6 evaluating the anti-thrombotic effect of the composition 100, which is obtained from the example 3 in accordance with an exemplary embodiment of the present invention.

Test subjects: the experiment was performed on healthy adult Wistar white rats; the quantity used was 30 rats, both male and female, weighing 180-210 g/rats. They were nurtured to stabilize for 1 week before conducting the experiment at room temperature (27° C.-28° C.). They were fed with synthetic pellets for mice, and the drinking water was tap water.

Experimental design: The white rats were randomly divided into 3 plots of 10 rats each.

Plot 1: (biology control): no impact;

Plot 2: apply voltaren 0.2 g/l rat foot; and

Plot 3: apply the composition 100 0.2 g/l rat foot.

The rats were treated with the drug 5 times for 3 consecutive days. The first day, 1 hour after applying the test samples, inflammation was induced by injecting 0.25 ml/mouse of 1% carrageenin (dissolved in saline) into the right hind paw of the mouse.

Measure the volume of the rat (up to the ankle joint) using a plethysmometer at the following times: before induce inflammation (V0), 1 hour after induce inflammation (V1), 2 hours (V2), 4 hours (V3) and 6 hours (V4), 24 hours (V5), 30 hours (V6) and 48 hours (V7).

The paw edema volume results are calculated using Fontaine's formula.

The increase in paw edema volume of each rat was calculated according to the formula:

$$\Delta V \text{ \% hour} = \frac{V_t - V_0}{V_0} \times 100$$

wherein: $\Delta V$ % is the increase in paw edema volume;

$V_0$ is the increase in paw edema volume before induce inflammation;

$V_t$ is the increase in paw edema volume after induce inflammation;

The anti-inflammatory effect of the test samples is evaluated by the ability to inhibit edema response (1%) according to the formula:

$$I \text{ \%} = \frac{\Delta V_c \text{ \%} - \Delta V_t \text{ \%}}{\Delta V_0 \text{ \%}} \times 100$$

wherein: $\Delta V$ % is average increase in edema volume of the rat's paw in the control group $\Delta V_t$% is average increase in edema volume of the rat's paw in the apply the composition 100

Measure the thickness of the rat's paw: one technician holds the mouse still. Another person places a ruler on the thickest part of the rat's paw. When the two edges of the ruler touch the rat's paw, the electronic screen will display the measurement in mm at the following times: before Induce inflammation (V0); 1 hour after Induce inflammation (V1), 2 hours (V2), 4 hours (V3) and 6 hours (V4), 24 hours (V5), 30 hours (V6) and 48 hours (V7).

The calculation of the % increase in thickness is similar to the paw edema volume according to the formula:

$$\Delta D \text{ \%} = \frac{D_t - D_0}{D_0} \times 100$$

wherein: $\Delta D$ % is the increase in thickness;

$D_0$ is the increase in thickness of the rat's paw before induce inflammation;

$D_t$ is the increase in thickness of the rat's paw after induce inflammation;

The anti-inflammatory effect of the test samples is evaluated by the ability to inhibit edema response (1%) according to the formula:

$$I\% = \frac{\Delta D_c\% - \Delta D_t\%}{\Delta D_0\%} \times 100$$

wherein: $\Delta D\%$ is average increase in thickness of the rat's paw in the control group $\Delta V_t\%$ is average increase in thickness of the rat's paw in the apply the composition 100

The Result

The Edema Volume of the Rat's Paw

TABLE 9

Anti-inflammatory effect of the composition 100 on inducing paw edema in rat model through the edema volume of the rat's paw index

| Plot | n | after 1 hour | after 2 hours | after 4 hours | after 6 hours | after 24 hours | after 30 hours | after 48 hours |
|---|---|---|---|---|---|---|---|---|
| Plot 1: biology control | 10 | 14.56 | 35.82 | 47.86 | 27.88 | 13.96 | 16.68 | 15.64 |
| Plot 2: apply voltaren 0.2 g/l rat foot | 10 | 4.86 | 6.95 | 22.84 | 8.94 | 5.87 | 4.82 | 2.43 |
| Plot 3: apply the composition 100 0.2 g/l rat | 10 | 12.45 | 14.44 | 25.78 | 11.79 | 7.98 | 6.83 | 4.96 |

Based on Table 9 shows that: The increase in paw edema volume at the following times after inducing inflammation in the test samples-use group was significantly lower than that of the biological control. Specifically, after 48 hours of the test samples use, it was found that the group applying the composition 100 and the group applying voltaren at a concentration of 0.2 g/l rat paw had an increase in mouse paw volume of 4.96% and 2.43%, significantly lower than the biological control group not using the drug at 15.64%.

The Thickness of the Rat's Paw

TABLE 10

Anti-inflammatory effect of the composition 100 on inducing paw edema in rat model through the thickness of the rat's paw

| Plot | n | after 1 hour | after 2 hours | after 4 hours | after 6 hours | after 24 hours | after 30 hours | after 48 hours |
|---|---|---|---|---|---|---|---|---|
| Plot 1: biology control | 10 | 85.67 | 97.53 | 105.27 | 90.41 | 69.14 | 60.26 | 30.65 |
| Plot 2: apply voltaren 0.2 g/l rat foot | 10 | 57.74 | 61.68 | 68.34 | 58.29 | 49.48 | 39.88 | 15.67 |
| Plot 3: apply the composition 100 0.2 g/l rat | 10 | 81.65 | 83.76 | 90.16 | 81.33 | 58.34 | 46.13 | 17.62 |

Based on Table 10 shows that: The increase in thickness of the rat's paw at the following times after inducing inflammation was the smallest in the Voltaren group (15.67%) and the composition 100 group (17.62%), which was significantly lower than the biological control group (30.65%). The composition 100 group had a change in the increase in paw thickness.

In short, both indexes of paw edema and thickness of the rat's paw gave similar results: reduced paw edema volume and thickness of the rat's paw in the group applying the composition 100 and the group applying voltaren. Thus, composition 100 has an anti-inflammatory effect on the carrageen-induced inflammation model of the white rat paw.

The example 7 evaluating the pain relief effect of the composition 100, which is obtained from the example 3 in accordance with an exemplary embodiment of the present invention.

Test subjects: the experiment was performed on healthy adult (Swiss albino) white mice, the quantity used was 40 rats, both male and female, 5-6 weeks old, weighing 20+2 grams. They were nurtured to stabilize for 1 week before conducting the experiment at room temperature (27° C.-28° C.). They were fed with synthetic pellets for mice, and the drinking water was tap water.

Experimental design: The white mice were randomly divided into 4 plots of 10 rats each.

Plot 1: (biology control): do not apply to the mouse's feet;

Plot 2: apply salonpas gel to the entire soles of the mouse's feet;

Plot 3: apply voltaren to the entire soles of the mouse's feet; and

Plot 4: apply the composition 100 to the entire soles of the mouse's feet.

After 30 minutes from the time of application, the mice were measured for pain response using the hot plate method.

The measurement method is as follows: Place the mouse on the hot plate, which is always maintained at 56° C. by a thermostat. The reaction time to thermal stimulation was calculated from the time the mouse was placed on the hot plate until the mouse had a reflex to licking and/or shaking its hind paw. Removed mice that respond too quickly (before 8 seconds) or too slowly (after 30 seconds). Comparison of response times to thermal stimuli before and after the test samples application and comparison between plots of mice.

The Result

TABLE 11

Effect of the composition 100 on temperature reaction time of white mice

| Plot | n | Pain response time (seconds) |
|---|---|---|
| Plot 1 biology control | 10 | 4.24 |
| Plot 2 (Salonpas gel) | 10 | 5.37 |
| Plot 3 (Voltaren) | 10 | 5.21 |
| Plot 4 (the composition 100) | 10 | 6.46 |

Based on Table 11 shows that: all control samples showed the effect of prolonging the time to the appearance of pain response compared with the control plot. The time to appearance of pain response of plot biology control was 4.24 seconds, while the plot using the composition 100 had the effect of prolonging the time to appearance of pain response by 6.46 seconds, more than the control samples salonpas gel was 5.37 seconds and voltaren 5.21 was seconds. Thus, composition 100 had the effect of reducing pain in white mice using the hot plate method.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A process of manufacturing a plant-based extract complex composition having the properties for supporting the relief of musculoskeletal pain, antibacterial and anti-inflammatory comprising:

(i) preparing material including: (A) a ginseng extract solution having a first percentage (%) by weight, (B) a medicinal herbs extract solution having a second percentage (%) by weight, (C) a plant-derived nanovesicles ingredient having a third percentage (%) by weight, (D) a plant-derived essential oils ingredient having a fifth percentage (%) by weight, (E) a methyl salicylate component having a fourth percentage (%) by weight, (F) an excipients component having a sixth percentage (%) by weight, and (G) water;

wherein the total percentage by weight of the composition is determined by the sum of the first to sixth percentages plus the percentage of water to make up 100% by weight of the plant-based extract complex composition;

wherein the ginseng extract solution is extracted from parts of ginseng, including roots, stems, leaves, and flowers that have been cleaned, then crushed or chopped and soaked in solvent or saline solution;

the roots have a minimum age of 5 years old; stems, leaves, and flowers of ginseng have a minimum age of 3 years old;

the ginseng parts are selected from one or more parts of plants belonging to the genus *Panax*, the *Panax* species being selected from the group consisting of: *Panax notoginseng, Panax bipinnatifidus, Korean ginseng, Panax Ginseng, Panax japonicus, American ginseng, Panax quonquefolius, Ngoc Linh ginseng, Panax vietnamensis, Panax wangianus, Panax zingiberebsis, Panax pseudoginseing,* and *Panax stipuleanatus;* wherein the medicinal herbs extract solution is prepared by performing steps (a1) to (a3):

(a1) collecting and pre-processing material from medicine herbals (a)-(l) including removing damaged parts, washing, and drying to 8%-15% moisture, chopping and stored in separate instruments;

wherein material from medicine herbals (a)-(l) include: (a) the flower of *Carhamus tinctorius* L., (b) the resin from the fruit and stem of *Daemonorops draco* (Willd.) Blume, (c) the roots and tubers of *Coptis chinensis* Franch., (d) the roots and tubers of *Reynoutria japonica* Houtt., (e) the bark of *Carhamus tinctorius* L., (f) the tubers of *Zingiber officinale* Rosc., (g) the fruits of *Illicium verum* Hook. f. *Illicium verum*, (h) the whole plant of *Piper sarmentosum*, (i) the leaves of *Artemisia vulgaris*, (j) the tubers of Codonopsis *pilosula* Nannf, (k) the flower buds of *Flos caryophylatac*, and (l) the seeds of *Brassica alba;*

(a2) creating a medicine herbals mixture by performing steps (a') to (b'):

(a') collecting and pre-processing material from medicine herbals (m)-(n) including removing damaged parts, washing, drying overnight exposed to dew and drying to 8%-15% moisture, chopping and stored in separate instruments; wherein the material from medicine herbals (m)-(n) include: (m) *Salvia miltiorrhiza* and (n) *Achyranthes bidentate* uses the roots; and (b') mixing the material from medicine herbals (a)-(l) prepared in step (a1) and the material from medicine herbals (m)-(n) prepared in step (a') to obtain the medicine herbals mixture; and (a3) soaking the medicine herbals mixture with 70% ethanol solvent in a ratio of 18:70 w/v at room temperature, stirring at a frequency of 200-250 rpm for 10 days to obtain a mixture 1, filtering the mixture 1 to obtain a filtrate 1 and residue 1; soaking the residue 1 with 70% ethanol solvent in a ratio of 18:70 w/v, stirring at a frequency of 200-250 rpm for 10 days to obtain a mixture 2, filtering the mixture 2 to obtain a filtrate 2 and residue 2; soaking the residue 2 with 70% ethanol solvent in a ratio of 18:70 w/v, stirring at a frequency of 200-250 rpm for 10 days to obtain a mixture 3, filtering the mixture 3 to obtain a filtrate 3 and a residue 3; mixing the filtrate 1 with the filtrate 2, and filtrate 3 to obtain a filtrate mixture, removing the solvent from the filtrate mixture by vacuum evaporation at 40° C.-45° C. to obtain the medicinal herbs extract solution;

wherein the plant-derived nanovesicles ingredient is prepared by mixing a first nanovesicles ingredient with a second nanovesicles ingredient in a ratio of 2:3 w/w;

the first nanovesicles ingredient is prepared by performing steps (b1) to (b8):

(b1) collecting the material from plants in the following percentage (%) by weight including 2 parts of *Ilicium verum* Hook. f. *Illicium verum,* 3 parts of *Artemisia vulgaris*, and 3 parts of *Piper sarmentosum* to obtain a temporary mixture;

(b2) washing the temporary mixture three times with deionized water at 20° C. 25° C.;

(b3) pureeing the washed temporary mixture with phosphate buffer solution (PBS) in a ratio of 1:3 w/v at a speed of 7,000-8,000 rpm for 15 minutes to obtain a first temporary solution;

(b4) filtering the first temporary solution by a filter membrane with a diameter 0.20-0.22 μm to obtain a second temporary solution;

(b5) centrifuging the second temporary solution by ultracentrifugation at 120,000×g for 100 min at 4° C. to obtain a temporary residue;

(b6) dissolving the temporary residue in phosphate buffer solution (PBS), transferring to a 45% sucrose gradient solution, and ultracentrifuging at 130,000×g for 100 min to obtain a third temporary solution;

(b7) washing the third temporary solution with PBS and centrifuging at 150.000×g for 60 min at 4° C. to obtain a fourth temporary solution; and (b8) filtering the fourth temporary solution through a filter membrane with a diameter 0.20-0.22 μm to obtain the first nanovesicles ingredient;

the second nanovesicles ingredient is prepared by performing steps (c1) to (c9):

(c1) collecting a fruit mixture in the following percentage (%) by weight including 3 parts of dragon fruit (*Hylocereus undatus, Hylocereus costaricensis, Hylocereus megalanthus, Hylocereus undatus costaricensis*), 3 parts of avocado (*Persea americana*), and 1 part of watermelon (*Citrullus lanatus*);

(c2) washing the fruit mixture three times with deionized water at 20° C.-25° C.;

(c3) pureeing the washed fruit mixture with phosphate buffer solution (PBS) in a ratio of 1:1 (g/mL) at a speed of 7,000-8,000 rpm for 15 minutes to obtain a first foundation solution;

(c4) filtering the first foundation solution by a filter membrane with a diameter 0.20-0.22 μm to obtain a second foundation solution;

(c5) centrifuging the second foundation solution by ultracentrifugation at 100,000×g for 60 min to obtain a residue;

(c6) dissolving the residue in phosphate buffer solution (PBS), transferring to a 45% sucrose gradient solution, and ultracentrifuging at 130,000×g for 100 min to obtain a third foundation solution;

(c7) stirring the third foundation solution with a 10% polyethylene glycol-8000 (PEG8000) solution in a ratio of 1:1 v/v, and incubating for 8-10 hours at 4° C., then centrifuging at 110,000×g for 40 minutes at 4° C. to obtain a precipitate;

(c8) dissolving the precipitate in phosphate buffer solution (PBS) in a ratio of 1:2 w/v to obtain a foundation solution; and (c9) filtering the foundation solution by a tangential flow filtration (TFF) to obtain the second nanovesicles ingredient; wherein the technical specifications related to TFF include a molecular size of 500 kDa, and filtering at a flow rate of 20 mL/min with the transmembrane pressure maintained at 2 bar;

wherein the plant-derived essential oils ingredient is prepared by mixing an essential oil of cajeput leaf, an essential oil of camphor leaf, an essential oil of cinnamon leaf, an essential oil of *eucalyptus* leaf, an essential oil of rosemary leaf, an essential oil of peppermint leaf, an essential oil of *perilla* leaf, and an essential oil of ginger rhizome n the respective mass ratios of (1-2):2:1:(1-2):2:1:(1-2):1;

wherein each plant-derived essential oils ingredient is extracted by performing steps (d1) to (d3):

(d1) collecting and pre-processing material from plant individually including removing damaged parts, washing, chopping, and soaking with an enzyme solution in a ratio of 1:2 w/v for 30 minutes, and filtering to obtain an enzyme-treated plant material;

in which the enzyme solution is prepared by:

creating an enzyme composition by mixing a cellulase with hemicellulase, and xylanase in a ratio of 1:1:1 w/w/w; and dissolving the enzyme composition with water in a ratio of 1:15000 w/v;

(d2) grinding a mixture of 1 part the enzyme-treated plant material with 7 parts saturated salt solution, let stand after grinding for 1 hour with microwave assistance at a power of 300-500 W, then steam distillation for 3 hours to obtain a crude essential oil; and (d3) removing water from the crude essential oil by adding $Na_2SO_4$ salt to crystallize at $-15°$ C., and filtering to obtain the plant-derived essential oils ingredient wherein the methyl salicylate component is synthesized by:

dissolving 1.5 g of salicylic acid (10 mmol) with 4.35 mL of 10% methanol in a 250 mL three-necked flask, adding 0.27 mL of 10% $H_2SO_4$, and refluxing at 82° C.-83° C. for 6 hours;

evaporating by rotary vacuum evaporation of the mixture after reaction at 62° C.-65° C. to remove the solvent, cooling the mixture after evaporation and putting it in a decanter;

coating the rotary vacuum evaporation flask with saturated $NaHCO_3$ solution put it in the decanter, adding 7 mL of saturated $NaHCO_3$ to the decanter, gently shaking the decanter then let it stand to obtain a lower solution layer;

washing the lower solution layer three times with saturated $NaHCO_3$ solution, wherein each time washing with saturated $NaHCO_3$ solution is 7 mL;

washing the lower solution layer three times with distilled water, wherein each time washing with distilled water is 12 mL;

adding 0.5 g of anhydrous $Na_2SO_4$ into the reaction mixture, filtering, and distilling fractional to obtain the methyl salicylate component at temperature of 220° C.;

wherein the excipients component is selected from the group consisting of ethanol, polysorbate 60, sorbitan oleate, triethanolamine, carbomer or combinations thereof;

(ii) obtaining a plant-based extract complex composition by mixing in a specific order into a container including (A) a ginseng extract solution having a first percentage (%) by weight, (B) a medicinal herbs extract solution having a second percentage (%) by weight, (C) a plant-derived nanovesicles ingredient having a third percentage (%) by weight, (D) a plant-derived essential oils ingredient having a fifth percentage (%) by weight, (E) a methyl salicylate component having a fourth percentage (%) by weight, (F) an excipients component having a sixth percentage (%) by weight, and (G) water to create a mixture; wherein after each addition of the mixing ingredients to the mixture is stirred until the mixture is homogeneous; and (iii) filling and packaging.

2. The process of claim 1, wherein the properties for supporting the relief of musculoskeletal pain, antibacterial and anti-inflammatory depend on the percentage (%) by weight of each ingredients (A)-(G) including a first formula, a second formula, a third formula, and a fourth formula;

wherein the third formula is stronger than the first formula, the first formula is stronger than the second formula, and the second formula is stronger than the fourth formula; in which the comparative factor is properties for supporting the relief of musculoskeletal pain, antibacterial and anti-inflammatory.

3. The process of claim 2, wherein the first formula comprises:

(A) the ginseng extract solution having 0.01%-0.5% by weight;

(B) the medicinal herbs extract solution having 12%-55% by weight;

(C) the plant-derived nanovesicles ingredient having 5%-10% by weight;

(D) the plant-derived essential oils ingredient having 10%-28% by weight;

(E) the methyl salicylate component having 0.001%-0.8% by weight;

(F) the excipient component having 0.001%-5% by weight; and (G) the remainder is the water.

4. The process of claim 2, wherein the second formula comprises:

(A) the ginseng extract solution having 0.01%-0.5% by weight;

(B) the medicinal herbs extract solution having 0.1%-12% by weight;

(C) the plant-derived nanovesicles ingredient having 1%-5% by weight;

(D) the plant-derived essential oils ingredient having 28%-48% by weight;

(E) the methyl salicylate component having 0.8%-10% by weight;

(F) the excipient component having 0.001%-5% by weight; and (G) the remainder is the water.

5. The process of claim 2, wherein the third formula comprises:

(A) the ginseng extract solution having 0.01%-0.5% by weight;

(B) the medicinal herbs extract solution having 12%-55% by weight;

(C) the plant-derived nanovesicles ingredient having 5%-10% by weight;

(D) the plant-derived essential oils ingredient having 28%-48% by weight;

(E) the methyl salicylate component having 0.8%-10% by weight;

(F) the excipient component having 0.001%-5% by weight; and (G) the remainder is the water.

6. The process of claim 2, wherein the fourth formula comprises:

(A) the ginseng extract solution having 0.01%-0.5% by weight;

(B) the medicinal herbs extract solution having 0.1%-12% by weight;

(C) the plant-derived nanovesicles ingredient having 1%-5% by weight;

(D) the plant-derived essential oils ingredient having 28%-48% by weight;

(E) the methyl salicylate component having 0.001%-0.8% by weight;

(F) the excipient component having 0.001%-5% by weight; and (G) the remainder is the water.

* * * * *